(12) United States Patent
Tan et al.

(10) Patent No.: US 11,077,193 B2
(45) Date of Patent: Aug. 3, 2021

(54) NERVE GROWTH FACTOR COMPOSITION AND POWDER INJECTION

(71) Applicants: STAIDSON (BEIJING) BIOPHARMACEUTICALS CO., LTD., Beijing (CN); BEIJING STAIDSON MEDICAL TECHNOLOGY CO., LTD., Beijing (CN)

(72) Inventors: Jianping Tan, Beijing (CN); Bingzhang Wang, Beijing (CN)

(73) Assignees: STAIDSON (BEIJING) BIOPHARMACEUTICALS CO., LTD., Beijing (CN); BEIJING STAIDSON MEDICAL. TECHNOLOGY CO.. LTD., Beijing (CN)

( * ) Notice: Subject to any disclaimer, the term of this patent is extended or adjusted under 35 U.S.C. 154(b) by 13 days.

(21) Appl. No.: 15/568,455

(22) PCT Filed: Apr. 18, 2016

(86) PCT No.: PCT/CN2016/079571
§ 371 (c)(1),
(2) Date: Jan. 31, 2018

(87) PCT Pub. No.: WO2016/169454
PCT Pub. Date: Oct. 27, 2016

(65) Prior Publication Data
US 2018/0161436 A1    Jun. 14, 2018

(30) Foreign Application Priority Data

Apr. 21, 2015 (CN) .......................... 201510189156.3

(51) Int. Cl.
| | | |
|---|---|---|
| *A61K 47/26* | (2006.01) | |
| *A61K 47/36* | (2006.01) | |
| *A61K 9/19* | (2006.01) | |
| *A61K 38/18* | (2006.01) | |
| *A61K 9/08* | (2006.01) | |
| *A61P 25/00* | (2006.01) | |
| *A61K 9/00* | (2006.01) | |
| *A61K 47/18* | (2017.01) | |

(52) U.S. Cl.
CPC ............ *A61K 47/26* (2013.01); *A61K 9/0019* (2013.01); *A61K 9/08* (2013.01); *A61K 9/19* (2013.01); *A61K 38/18* (2013.01); *A61K 38/185* (2013.01); *A61K 47/183* (2013.01); *A61K 47/36* (2013.01); *A61P 25/00* (2018.01)

(58) Field of Classification Search
None
See application file for complete search history.

(56) References Cited

U.S. PATENT DOCUMENTS 6,277,828 B1     8/2001   Knepp et al.
2003/0203040 A1* 10/2003  Cleland ............... A61K 9/1647
                                                    424/490

FOREIGN PATENT DOCUMENTS

| CN | 1552440 A | 12/2004 |
|---|---|---|
| CN | 1824297 A | 8/2006 |
| CN | 1857718 A | 11/2006 |
| CN | 101461786 A | 6/2009 |
| CN | 101972224 A | 2/2011 |
| WO | 1552440 | * 12/2004 |
| WO | 2007073035 A1 | 6/2007 |

OTHER PUBLICATIONS

Hadi et al, Natural surfactants, downloaded on Feb. 16, 2019 from <http://irep.iium.edu.my/14524/1/CHAPTER_10_Natural_surfactants_for_pharmaceutical_emulsions.pdf>, pp. 1-18.*
Paik et al (Am Inst Chem Eng Biotech Prog 28: 1517-1525, 2012).*
Russ, Intermed Physics Med Biol, 1-3. (Year: 2017).*
ISA State Intellectual Property Office of the People's Republic of China, International Search Report Issued in Application No. PCT/CN2016/079571, dated Jul. 13, 2016, WIPO, 9 pages.

* cited by examiner

*Primary Examiner* — Kimberly Ballard
*Assistant Examiner* — Aditi Dutt
(74) *Attorney, Agent, or Firm* — McCoy Russell LLP

(57) ABSTRACT

The present invention discloses nerve growth factor composition and an injection powder comprising the following components: 10 μg/mL-100 μg/mL of a nerve growth factor; 10 mg/mL-80 mg/mL of disaccharide stabilizer; 0 mg/mL-30 mg/mL of an amino acid stabilizer; 0.01 mg/mL-1 mg/mL of surfactant, 10 mg/mL-50 mg/mL of a supporting agent; a pH buffer for maintaining the nerve growth factor composition at 6.0-7.4, and solvent being water. The nerve growth factor composition and the injection powder can avoid the potential risk resulting from the virus of other unknown components carried in albumin by using a disaccharide or a combination of a disaccharide and an amino acid instead of albumin as a stabilizer; not only have protective effect on mNGF, but also can ensure the stability of hNGF and rhNGF in the preparation, transportation and storage processes, and have better medication safety and quality control.

12 Claims, 2 Drawing Sheets

NERVE GROWTH FACTOR COMPOSITION AND POWDER INJECTION

CROSS-REFERENCE TO RELATED APPLICATIONS

The present application is a U.S. National Phase of International Patent Application Serial No. PCT/CN2016/079571, entitled "NERVE GROWTH FACTOR COMPOSITION AND POWDER INJECTION," filed on Apr. 18, 2016. International Patent Application Serial No. PCT/CN2016/079571 claims priority to Chinese Patent Application No. 201510189156.3, filed on Apr. 21, 2015. The entire contents of each of the above-cited applications are hereby incorporated by reference for all purposes.

TECHNICAL FIELD

The present invention relates to a nerve growth factor composition and an injection powder, and belongs to the field of pharmaceutical biology.

BACKGROUND ART

Nerve growth factor (NGF) is a nerve cell growth regulator with the double biological functions of neuronal nutrition and neurite growth promotion, and it has an important regulatory effect on the development, differentiation, growth, regeneration and functional property expression of the central and peripheral neurons. NGF contains three subunits, α, β, γ, wherein the β subunit is an active region, formed by two single chains composed of 118 amino acids by a non-covalent bond. In 1953, the Italian scientist Levi-Montalcini discovered NGF and won the Nobel Prize. At present, there are a number of NGF products which appear on the market all over the world, and they are clinically used mainly for the treatment of neurological dysplasia, including amblyopia, neuroma, various nerve injury and neurological diseases and other diseases.

NGF is similar to other proteins; since the protein has a short half life, the spatial conformation of the protein easily changes and thus results in protein denaturation when exposed to extreme temperature and humidity conditions, or by influenced by physical and chemical factors; the denaturated protein will lose its original biological activity; in addition, because the protein often tends to adhere to a solid surface, in the container filling process, part of the protein will adhere to the inner wall of the container, resulting in the loss of active ingredients. In order to ensure its biological activity, there is a need to add a stabilizer to prevent the loss of the biological activity.

Generally, albumin is widely used in various biological products as an excellent stabilizer and as a cake forming agent. However, since albumin is mainly derived from human blood, placental blood, and the blood may carry some of the unknown components which are not easy to be detected, the NGF composition as a non-sterile preparation which is sterilized, may easily be contaminated; at the same time, the long-term and wide applications of albumin are also susceptible to blood supply constraints and production costs; again, in the determination of the contents of the intermediates and preparation of finished product, albumin may interfere with a relatively small amount of NGF and thus affect the product quality management. Therefore, in order to avoid the above problems, it is necessary to find a stable albumin-free NGF composition.

SUMMARY OF THE INVENTION

It is an object of the present invention to provide a nerve growth factor composition and an injection powder which not only protect mouse-derived nerve growth factor (mNGF) but also can ensure the good stability of human-derived nerve growth factor (hNGF) and recombinant human nerve growth factor (rhNGF) in the preparation, transportation and storage processes, and have better clinical medication safety and quality controllability.

The present invention provides a nerve growth factor composition comprising the following components:
- a nerve growth factor at a mass-volume concentration of 10 μg/mL-100 μg/mL;
- a disaccharide stabilizer at a mass-volume concentration of 10 mg/mL-80 mg/mL;
- an amino acid stabilizer at a mass-volume concentration of 0 mg/mL-30 mg/mL;
- a surfactant at a mass-volume concentration of 0.01 mg/mL-1 mg/mL of;
- a supporting agent at a mass-volume concentration of 10 mg/mL-50 mg/mL;
- a pH buffer for maintaining said nerve growth factor composition at a pH value of 6.0 to 7.4;
- a solvent being water.

The addition of a stabilizer in the above nerve growth factor composition avoids or reduces the aggregation and depolymerization of proteins caused in the preparation or storage process, and the term "stabilizer" refers to a substance which prevents the active ingredient from aggregating or depolymerizing in an aqueous solution, and in addition to the function of stability, the stabilizer can also be used as a supporting agent to improve the product formability, with other functions being not excluded;

In the above nerve growth factor composition, preferably, the mass-volume concentration of said disaccharide stabilizer is 30 mg/mL-70 mg/mL, and more preferably, the mass-volume concentration of said disaccharide stabilizer is 30 mg/mL;

In the above nerve growth factor composition, said disaccharide stabilizer may be at least one of maltose, trehalose, sucrose and lactose;

In the above nerve growth factor composition, preferably, the mass-volume concentration of said amino acid stabilizer is 2 mg/mL-10 mg/mL, and more preferably, the mass-volume concentration of said amino acid stabilizer is 3 mg/mL-10 mg/mL, and still preferably, the mass-volume concentration of said amino acid stabilizer is 3 mg/mL, 10 mg/mL.

In the above nerve growth factor composition, said amino acid stabilizer may be at least one of alanine, glycine, arginine, glutamic acid, histidine and isoleucine.

In the above nerve growth factor composition, said disaccharide stabilizer and said amino acid stabilizer may specifically be any one of the following 1) to 8):
sucrose and histidine, 2) sucrose and glycine, 3) sucrose, glycine and histidine, 4) lactose and glycine, 5) lactose, sucrose and isoleucine, 6) trehalose, arginine and histidine, 7) maltose, glycine and histidine, 8) maltose, alanine, arginine and glutamic acid.

In the above nerve growth factor composition, since the protein has a high tendency to interact with a surface, it is susceptible to adsorption and/or denaturation at a gas-liquid, bottle-liquid interface, which is inversely proportional to the protein concentration, and leads to the formation of soluble and insoluble protein aggregates, or the loss of protein in the solution by adsorption to the interface. The addition of the surfactant can prevent the adsorption and/or denaturation initiated by the solution surface interactions such that the adsorption and/or denaturation caused by the surface is minimized. This is because the surfactant is an amphoteric molecule that can compete with the protein at the interface position, and the hydrophobic portion of the surfactant molecule occupies the interface position (e.g., gas-liquid), while the hydrophilic portion of the molecule remains directed to the solvent bulk; at a sufficient concentration (usually around the critical micelle concentration of the surfactant), the surface layer of the surfactant molecule acts to prevent the adsorption of protein molecules at the interface;

in the above nerve growth factor composition, preferably, the mass-volume concentration of said surfactant is 0.1 mg/mL-0.5 mg/mL, and more preferably, the mass-volume concentration of said surfactant is 0.2 mg/mL-0.5 mg/mL, and still preferably, the mass-volume concentration of said surfactant is 0.2 mg/mL, 0.5 mg/mL;

in the above nerve growth factor composition, said surfactant may be a nonionic surfactant, and preferably said nonionic surfactant may be at least one of poloxamer, polysorbate and 15-polyethleneglycol hydroxystearate (abbreviated as HS 15, the same below), and in particular may be any one of poloxamer, polysorbate and HS 15.

In the above nerve growth factor composition, the addition of said supporting agent can improve the appearance of the finished product and ensure that the product has good formability after lyophilization;

in the above nerve growth factor composition, preferably, the mass-volume concentration of said supporting agent is 20-50 mg/mL, and more preferably, the mass-volume concentration of said supporting agent is 20 mg/mL, 50 mg/mL;

in the above nerve growth factor composition, said supporting agent may be any of mannitol, dextrin and dextran.

In the above nerve growth factor composition, in order to ensure that the composition has the greatest biological activity, it is generally necessary to control an optimum pH range. The optimum pH range for this stability needs to be determined at the time of formulation screening, usually using an influencing factor test (illumination, high temperature, high humidity), accelerated and long-term stability tests and other methods. After the determination of the formulation, the composition in the production and storage processes must be maintained at its optimum pH range. Since the pH buffer has good buffering capacity, the relative stability of the product pH can be maintained in a certain range; therefore, a buffer is often added for the control of pH value in the formulation;

in the above nerve growth factor composition, the molar concentration of said pH buffer is 10 mM-50 mM, preferably, the molar concentration of said pH buffer is 20 mM-25 mM, and more preferably, the molar concentration of said pH buffer is 20 mM, 25 mM;

in the above nerve growth factor composition, preferably, said nerve growth factor composition is maintained at pH value of 6.80-7.00, more preferably, said nerve growth factor composition is maintained at pH value of 6.86-6.91, and still preferably, said nerve growth factor is maintained at pH value of 6.86, specifically 6.80, 6.82, 6.83, 6.85, 6.86, 6.87, 6.91, 6.92 or 7.00;

in the above nerve growth factor composition, the pH buffer is at least one of a phosphate, a citrate, an acetate, a histidine hydrochloride and an arginine hydrochloride, and may specifically be 1) a phosphate, 2) a citrate, 3) an acetate, 4) a histidine hydrochloride, or 5) a histidine hydrochloride and an arginine hydrochloride, wherein the molar ratio of the histidine hydrochloride to the arginine hydrochloride in the 5) may be 12:13.

In the above nerve growth factor composition, said water is water for injection.

In the above nerve growth factor composition, said nerve growth factor is a nerve cell growth regulator with the double biological functions of neuronal nutrition and neurite growth promotion, and it has an important regulatory effect on the development, differentiation, growth, regeneration and functional property expression of the central and peripheral neurons;

in the above nerve growth factor composition, preferably, the mass-volume concentration of said nerve growth factor is 40 µg/mL-60 µg/mL, more preferably the mass-volume concentration of said nerve growth factor is 50 µg/mL;

in the above nerve growth factor composition, said nerve growth factor is a mouse-derived nerve growth factor, a human-derived nerve growth factor, or a recombinant human nerve growth factor.

In the above nerve growth factor composition, the concentration of each component may be any one of the following 1) to 17):

1) the nerve growth factor: 40 µg/mL-80 µg/mL, the disaccharide stabilizer: 10 mg/mL-40 mg/mL, the amino acid stabilizer: 0 mg/mL-6 mg/mL, the surfactant: 0.01 mg/mL-0.2 mg/mL, the supporting agent: 10 mg/mL-30 mg/mL, the pH buffer: 10 mM-25 mM;

2) the nerve growth factor: 60 µg/mL-100 µg/mL, the disaccharide stabilizer: 40 mg/mL-80 mg/mL, the amino acid stabilizer: 6 mg/mL-30 mg/mL, the surfactant: 0.2 mg/mL-1 mg/mL, the supporting agent: 30 mg/mL-50 mg/mL, the pH buffer: 25 mM-50 mM;

3) the nerve growth factor: 10 µg/mL-50 µg/mL, the disaccharide stabilizer: 30 mg/mL-50 mg/mL, the amino acid stabilizer: 2 mg/mL-10 mg/mL, the surfactant: 0.05 mg/mL-0.4 mg/mL, the supporting agent: 20 mg/mL-40 mg/mL, the pH buffer: 20 mM-30 mM;

4) the nerve growth factor: 10 µg/mL-50 µg/mL, the disaccharide stabilizer: 35 mg/mL-70 mg/mL, the amino acid stabilizer: 3 mg/mL-13 mg/mL, the surfactant: 0.1 mg/mL-0.5 mg/mL, the supporting agent: 20 mg/mL-40 mg/mL, the pH buffer: 20 mM-30 mM;

5) the nerve growth factor: 10 µg/mL-50 µg/mL, the disaccharide stabilizer: 35 mg/mL-70 mg/mL, the amino acid stabilizer: 4 mg/mL-14 mg/mL, the surfactant: 0.1 mg/mL-0.5 mg/mL, the supporting agent: 20 mg/mL-40 mg/mL, the pH buffer: 20 mM-30 mM;

6) the nerve growth factor: 40 µg/mL-60 µg/mL, the disaccharide stabilizer: 30 mg/mL-70 mg/mL, the amino acid stabilizer: 0 mg/mL-10 mg/mL, the surfactant: 0.2 mg/mL-0.5 mg/mL, the supporting agent: 20 mg/mL-50 mg/mL, the pH buffer: 20 mM-25 mM;

7) the nerve growth factor: 40 µg/mL-60 µg/mL, the disaccharide stabilizer: 30 mg/mL-70 mg/mL, the amino acid stabilizer: 3 mg/mL-10 mg/mL, the surfactant: 0.2 mg/mL-0.5 mg/mL, the supporting agent: 20 mg/mL to 50 mg/mL, the pH buffer: 20 mM to 25 mM;

8) the nerve growth factor: 10 µg/mL, the disaccharide stabilizer: 10 mg/mL, the amino acid stabilizer: 0 mg/mL, the surfactant: 0.01 mg/mL, the supporting agent: 10 mg/mL, the pH buffer: 10 mM;

9) the nerve growth factor: 40 µg/mL, the disaccharide stabilizer: 30 mg/mL, the amino acid stabilizer: 2 mg/mL, the surfactant: 0.05 mg/mL, the supporting agent: 20 mg/mL, the pH buffer: 20 mM;

10) the nerve growth factor: 50 μg/mL, the disaccharide stabilizer: 35 mg/mL, the amino acid stabilizer: 3 mg/mL, the surfactant: 0.1 mg/mL, the supporting agent: 30 mg/mL, the pH buffer: 25 mM;

11) the nerve growth factor: 60 μg/mL, the disaccharide stabilizer: 40 mg/mL, the amino acid stabilizer: 4 mg/mL, the surfactant: 0.2 mg/mL, the supporting agent: 40 mg/mL, the pH buffer: 30 mM;

12) the nerve growth factor: 80 μg/mL, the disaccharide stabilizer: 50 mg/mL, the amino acid stabilizer: 6 mg/mL, the surfactant: 0.4 mg/mL, the supporting agent: 50 mg/mL, the pH buffer: 50 mM;

13) the nerve growth factor: 100 μg/mL, the disaccharide stabilizer: 70 mg/mL, the amino acid stabilizer: 10 mg/mL, the surfactant: 0.5 mg/mL, the supporting agent: 50 mg/mL, the pH buffer: 50 mM;

14) the nerve growth factor: 100 μg/mL, the disaccharide stabilizer: 80 mg/mL, the amino acid stabilizer: 13 mg/mL, the surfactant: 1 mg/mL, the supporting agent: 50 mg/mL, the pH buffer: 50 mM;

15) the nerve growth factor: 100 μg/mL, the disaccharide stabilizer: 80 mg/mL, the amino acid stabilizer: 14 mg/mL, the surfactant: 1 μg/mL, the supporting agent: 50 mg/mL, the pH buffer: 50 mM;

16) the nerve growth factor: 100 μg/mL, the disaccharide stabilizer: 80 mg/mL, the amino acid stabilizer: 30 mg/mL, the surfactant: 1 mg/mL, the supporting agent: 50 mg/mL, the pH buffer: 50 mM;

17) the nerve growth factor: 50 μg/mL, the disaccharide stabilizer: 30 mg/mL, the amino acid stabilizer: 3 mg/mL, the surfactant: 0.2 mg/mL, the supporting agent: 50 mg/mL, the pH buffer: 25 mM;

18) the nerve growth factor: 50 μg/mL, the disaccharide stabilizer: 30 mg/mL, the amino acid stabilizer: 10 mg/mL, the surfactant: 0.5 mg/mL, the supporting agent: 20 mg/mL, the pH buffer: 20 mM.

The present invention further provides a method for preparing the above nerve growth factor composition injection powder, wherein the above nerve growth factor composition is lyophilized to obtain the nerve growth factor composition injection powder.

It is another object of the present invention to provide a nerve growth factor composition injection powder prepared by the above method, for injection administration.

In the above nerve growth factor composition injection powders, the water content of the injection powders may be 1.2%-3.0%, specifically 1.3%, 1.7%, 1.9%, 2.2%, 2.3%, 2.4%, 2.5%, 2.7% or 2.8%; the pH value of the injection powders may be 6.80-7.20, specifically 6.80, 6.82, 6.83, 6.85, 6.92, 6.93, 6.95, 7.05, 7.10, 7.10 or 7.20.

The use of the above nerve growth factor compositions in the treatment of nerve injury or the preparation of a medicament for the treatment of nerve injury is also within the scope of the present invention. Said nerve growth factor composition may specifically be a nerve growth factor composition injection powder. The nerve injury may be an optic nerve injury, and the cause of the injury may be a first injury, a car accident, a physical hit injury or an eye explosive injury.

The present invention further provides a method of treating nerve injury comprising the step of: administering an effective amount of a nerve growth factor composition to a patient with the nerve injury. Said nerve growth factor composition may specifically be a nerve growth factor composition injection powder. The administration may specifically be intramuscular injection. The nerve injury may be an optic nerve injury, and the cause of the injury may be a first injury, a car accident, a physical hit injury or an eye explosive injury.

DETAILED DESCRIPTION OF EMBODIMENTS

Figure 1:
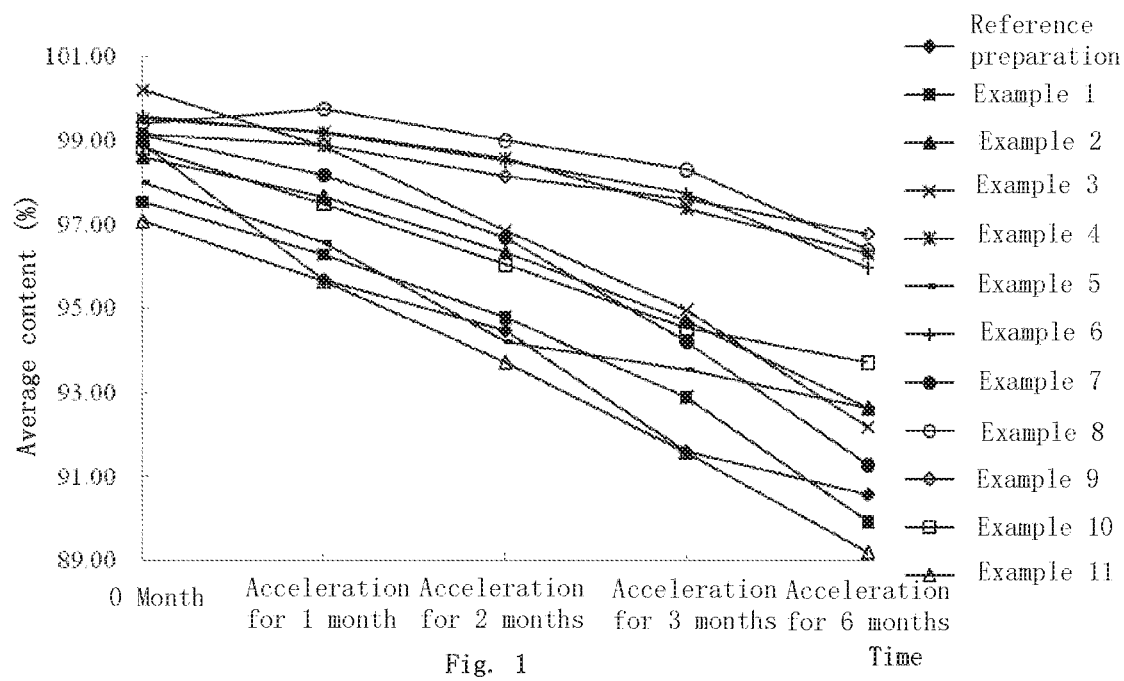
FIG. 1 shows the change curve of the average content of NGF over time in the NGF composition injection powders prepared in the Examples and the reference preparation, under the accelerated condition (25° C., RH 60±10%).

In order to provide a better understanding of the technical solution of the present invention to those skilled in the art, the present invention will be described in further detail with reference to examples and test examples, but these examples are not to be construed as limiting the present invention.

The experimental methods used in the following Examples are conventional methods unless otherwise specified.

The materials, reagents and the like used in the following Examples are commercially available, unless otherwise specified.

The mNGF and hNGF stock solutions used in the following Examples are supplied by the Staidson (Beijing) Biopharmaceuticals Co., Ltd., the rhNGF stock solution is supplied by the Sino Biological Inc., and the rest of the excipients are all injection grade unless otherwise specified.

The unit of concentration of the surfactant in the following Examples is expressed in %, such as 0.1% for 1 mg/mL.

In order to find a substitute for albumin as a stabilizer for NGF, in the present invention, a large number of exploratory experiments have been carried out, in which maltose, trehalose, sucrose, lactose, alanine, glycine, arginine, glutamic acid, histidine, isoleucine as a stabilizer for this product and polysorbate-20 (abbreviated as TW-20, the same below), polysorbate-80 (abbreviated as TW-80, the same below), poloxamer 188 (abbreviated as F68, the same below), HS 15 as a surfactant are used to prepare a variety of NGF compositions and injection powders, and the moisture, pH, osmotic pressure, content and activity of the finished products are determined.

Example 1. Preparation of NGF Composition and Injection Powder

The NGF composition and the injection powder are prepared as follows:

a formulation amount of a citrate is weighed according to the formulation composition in Table 1, an appropriate amount of water for injection is added and stirred to complete dissolution, then formulation amounts of trehalose, mannitol and F68 are added and stirred to complete dissolution, a hNGF stock solution is added, the pH is adjusted to pH 6.85 as shown in Table 1 with NaOH or citric acid, water for injection is added to the volume of the scale, after having been mixed uniformly, the mixture is filtered through a 0.22 µm microfiltration membrane into a sterile container to prepare a composition having an NGF concentration of about 80 µg/mL.

The above composition is subpackaged into a borosilicate glass injection bottle at 0.63±0.03 mL/bottle and lyophilized, to prepare a sterile powder for hNGF injection, i.e., a hNGF injection powder.

Example 2. Preparation of NGF Composition and Injection Powder

The NGF composition and the injection powder are prepared as follows:

a formulation amount of a phosphate is weighed according to the formulation composition in Table 1, an appropriate amount of water for injection is added and stirred to complete dissolution, then formulation amounts of sucrose, glycine, histidine and dextran are added and stirred to complete dissolution; since the TW-20 in the formulation is in a spherical aggregate state in the water for injection and is not easily mixed uniformly, TW-20 is firstly dissolved in hot water for injection (40° C.-80° C.) to formulate into an 1% aqueous solution, and after having been cooled to room temperature, it is added into the above solution in an amount converted from the formulation amount, and mixed uniformly in the present invention; finally, a rhNGF stock solution is added, the pH is adjusted to pH 7.00 as shown in Table 1 with NaOH or phosphoric acid, and water for injection is add to the volume of the scale, after having been mixed uniformly, the mixture is filtered through a 0.22 µm microfiltration membrane into a sterile container to prepare a composition having an NGF concentration of about 50 µg/mL.

The above composition is subpackaged into a borosilicate glass injection bottle at 0.63±0.03 mL/bottle and lyophilized, to prepare a sterile powder for rhNGF injection, i.e., a rhNGF injection powder.

Example 3. Preparation of NGF Composition and Injection Powder

The NGF composition and the injection powder are prepared as follows:

a formulation amount of an acetate is weighed according to the formulation composition in Table 1, an appropriate amount of water for injection is added and stirred to complete dissolution, then formulation amounts of maltose, alanine, arginine, glutamic acid and mannitol are added and stirred to complete dissolution; since the HS 15 in the formulation is in a spherical aggregate state in the water for injection and is not easily mixed uniformly, HS 15 is firstly dissolved in hot water for injection (40° C.-80° C.) to formulate into an 1% aqueous solution, and after having been cooled to room temperature, it is added into the above solution in an amount converted from the formulation amount, and mixed uniformly in the present invention; finally, a hNGF stock solution is added, the pH is adjusted to pH 6.92 as shown in Table 1 with NaOH or acetic acid, and water for injection is add to the volume of the scale, after having been mixed uniformly, the mixture is filtered through a 0.22 µm microfiltration membrane into a sterile container to prepare a composition having an NGF concentration of about 40 µg/mL.

The above composition is subpackaged into a borosilicate glass injection bottle at 0.63±0.03 mL/bottle and lyophilized, to prepare a sterile powder for hNGF injection, i.e., a hNGF injection powder.

Example 4. Preparation of NGF Composition and Injection Powder

The NGF composition and the injection powder are prepared as follows:

a formulation amount of a histidine hydrochloride is weighed according to the formulation composition in Table 1, an appropriate amount of water for injection is added and stirred to complete dissolution, then formulation amounts of sucrose, histidine and mannitol are added and stirred to complete dissolution; since the TW-20 in the formulation is in a spherical aggregate state in the water for injection and is not easily mixed uniformly, TW-20 is firstly dissolved in hot water for injection (40° C.-80° C.) to formulate into an 1% aqueous solution, and after having been cooled to room temperature, it is added into the above solution in an amount converted from the formulation amount, and mixed uniformly in the present invention; finally, a hNGF stock solution is added, the pH is adjusted to pH 6.87 as shown in Table 1 with HCl or L-histidine, and water for injection is add to the volume of the scale, after having been mixed uniformly, the mixture is filtered through a 0.22 µm microfiltration membrane into a sterile container to prepare a composition having an NGF concentration of about 60 µg/mL.

The above composition is subpackaged into a borosilicate glass injection bottle at 0.63±0.03 mL/bottle and lyophilized, to prepare a sterile powder for hNGF injection, i.e., a hNGF injection powder.

Example 5. Preparation of NGF Composition and Injection Powder

The NGF composition and the injection powder are prepared as follows:

a formulation amount of a citrate is weighed according to the formulation composition in Table 1, an appropriate amount of water for injection is added and stirred to complete dissolution, then formulation amounts of trehalose, sucrose mannitol are added and stirred to complete dissolution; since the TW-80 in the formulation is in a spherical aggregate state in the water for injection and is not easily mixed uniformly, TW-80 is firstly dissolved in hot water for injection (40° C.-80° C.) to formulate into an 1% aqueous solution, and after having been cooled to room temperature, it is added into the above solution in an amount converted from the formulation amount, and mixed uniformly in the present invention; finally, a mNGF stock solution is added, the pH is adjusted to pH 6.82 as shown in Table 1 with NaOH or citric acid, and water for injection is add to the volume of the scale, after having been mixed uniformly, the mixture is filtered through a 0.22 µm microfiltration membrane into a sterile container to prepare a composition having an NGF concentration of about 60 µg/mL.

The above composition is subpackaged into a borosilicate glass injection bottle at 0.63±0.03 mL/bottle and lyophilized, to prepare a sterile powder for mNGF injection, i.e., a mNGF injection powder.

Example 6. Preparation of NGF Composition and Injection Powder

The NGF composition and the injection powder are prepared as follows:

a formulation amount of a phosphate is weighed according to the formulation composition in Table 1, an appropriate amount of water for injection is added and stirred to complete dissolution, then formulation amounts of sucrose, glycine and mannitol are added and stirred to complete dissolution; since the TW-80 in the formulation is in a spherical aggregate state in the water for injection and is not easily mixed uniformly, TW-80 is firstly dissolved in hot water for injection (40° C.-80° C.) to formulate into an 1% aqueous solution, and after having been cooled to room temperature, it is added into the above solution in an amount converted from the formulation amount, and mixed uniformly in the present invention; finally, a hNGF stock solution is added, the pH is adjusted to pH 6.91 as shown in Table 1 with NaOH or phosphoric acid, and water for injection is add to the volume of the scale, after having been mixed uniformly, the mixture is filtered through a 0.22 μm microfiltration membrane into a sterile container to prepare a composition having an NGF concentration of about 50 μg/mL.

The above composition is subpackaged into a borosilicate glass injection bottle at 0.63±0.03 mL/bottle and lyophilized, to prepare a sterile powder for hNGF injection, i.e., a hNGF injection powder.

Example 7. Preparation of NGF Composition and Injection Powder

The NGF composition and the injection powder are prepared as follows:

a formulation amount of a histidine hydrochloride is weighed according to the formulation composition in Table 1, an appropriate amount of water for injection is added and stirred to complete dissolution, then formulation amounts of maltose, glycine, histidine and dextrin are added and stirred to complete dissolution; since the TW-80 in the formulation is in a spherical aggregate state in the water for injection and is not easily mixed uniformly, TW-80 is firstly dissolved in hot water for injection (40° C.-80° C.) to formulate into an 1% aqueous solution, and after having been cooled to room temperature, it is added into the above solution in an amount converted from the formulation amount, and mixed uniformly in the present invention; finally, a rhNGF stock solution is added, the pH is adjusted to pH 6.80 as shown in Table 1 with HCl or L-histidine, and water for injection is add to the volume of the scale, after having been mixed uniformly, the mixture is filtered through a 0.22 μm microfiltration membrane into a sterile container to prepare a composition having an NGF concentration of about 100 μg/mL.

The above composition is subpackaged into a borosilicate glass injection bottle at 0.63±0.03 mL/bottle and lyophilized, to prepare a sterile powder for rhNGF injection, i.e., a rhNGF injection powder.

Example 8. Preparation of NGF Composition and Injection Powder

The NGF composition and the injection powder are prepared as follows:

a formulation amount of a citrate is weighed according to the formulation composition in Table 1, an appropriate amount of water for injection is added and stirred to complete dissolution, then formulation amounts of trehalose, and mannitol are added and stirred to complete dissolution; since the HS 15 in the formulation is in a spherical aggregate state in the water for injection and is not easily mixed uniformly, HS 15 is firstly dissolved in hot water for injection (40° C.-80° C.) to formulate into an 1% aqueous solution, and after having been cooled to room temperature, it is added into the above solution in an amount converted from the formulation amount, and mixed uniformly in the present invention; finally, a hNGF stock solution is added, the pH is adjusted to pH 6.86 as shown in Table 1 with NaOH or citric acid, and water for injection is add to the volume of the scale, after having been mixed uniformly, the mixture is filtered through a 0.22 μm microfiltration membrane into a sterile container to prepare a composition having an NGF concentration of about 40 μg/mL.

The above composition is subpackaged into a borosilicate glass injection bottle at 0.63±0.03 mL/bottle and lyophilized, to prepare a sterile powder for hNGF injection, i.e., a hNGF injection powder.

Example 9. Preparation of NGF Composition and Injection Powder

The NGF composition and the injection powder are prepared as follows:

a formulation amount of a phosphate is weighed according to the formulation composition in Table 1, an appropriate amount of water for injection is added and stirred to complete dissolution, then formulation amounts of lactose, glycine and mannitol are added and stirred to complete dissolution; since the TW-20 in the formulation is in a spherical aggregate state in the water for injection and is not easily mixed uniformly, TW-20 is firstly dissolved in hot water for injection (40° C.-80° C.) to formulate into an 1% aqueous solution, and after having been cooled to room temperature, it is added into the above solution in an amount converted from the formulation amount, and mixed uniformly in the present invention; finally, a hNGF stock solution is added, the pH is adjusted to pH 6.86 as shown in Table 1 with NaOH or phosphoric acid, and water for injection is add to the volume of the scale, after having been mixed uniformly, the mixture is filtered through a 0.22 μm microfiltration membrane into a sterile container to prepare a composition having an NGF concentration of about 50 μg/mL.

The above composition is subpackaged into a borosilicate glass injection bottle at 0.63±0.03 mL/bottle and lyophilized, to prepare a sterile powder for hNGF injection, i.e., a hNGF injection powder.

Example 10. Preparation of NGF Composition and Injection Powder

The NGF composition and the injection powder are prepared as follows:

formulation amounts of a histidine hydrochloride and an arginine hydrochloride are weighed according to the formulation composition in Table 1, an appropriate amount of water for injection is added and stirred to complete dissolution, then formulation amounts of trehalose, arginine, histidine and mannitol are added and stirred to complete dissolution; since the TW-20 in the formulation is in a spherical aggregate state in the water for injection and is not easily mixed uniformly, TW-20 is firstly dissolved in hot water for injection (40° C.-80° C.) to formulate into an 1% aqueous solution, and after having been cooled to room temperature, it is added into the above solution in an amount converted from the formulation amount, and mixed uniformly in the present invention; finally, a rhNGF stock solution is added, the pH is adjusted to pH 6.83 as shown in Table 1 with HCl or L-histidine or L-arginine, and water for injection is add to the volume of the scale, after having been mixed uniformly, the mixture is filtered through a 0.22 μm microfiltration membrane into a sterile container to prepare a composition having an NGF concentration of about 60 μg/mL.

The above composition is subpackaged into a borosilicate glass injection bottle at 0.63±0.03 mL/bottle and lyophilized, to prepare a sterile powder for rhNGF injection, i.e., a rhNGF injection powder.

Example 11. Preparation of NGF Composition and Injection Powder

The NGF composition and the injection powder are prepared as follows:

a formulation amount of a phosphate is weighed according to the formulation composition in Table 1, an appropriate amount of water for injection is added and stirred to complete dissolution, then formulation amounts of lactose, sucrose, isoleucine, mannitol and F68 are added and stirred to complete dissolution, a mNGF stock solution is added, the pH is adjusted to pH 6.85 as shown in Table 1 with NaOH or phosphoric acid, water for injection is added to the volume of the scale, after having been mixed uniformly, the mixture is filtered through a 0.22 μm microfiltration membrane into a sterile container to prepare a composition having an NGF concentration of about 10 μg/mL.

The above composition is subpackaged into a borosilicate glass injection bottle at 0.63±0.03 mL/bottle and lyophilized, to prepare a sterile powder for mNGF injection, i.e., a mNGF injection powder.

TABLE 1

The amounts of components in Examples 1-11

| Formulation composition | Use | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|
| mNGF stock solution | Active Ingredient (μg/mL) | | | | | 60 | | | | | | 10 |
| hNGF stock solution | | 80 | | 40 | 60 | | 50 | | 40 | 50 | | |
| rhNGF stock solution | | | 50 | | | | | 100 | | | 60 | |
| maltose | stabilizer (mg/mL) | | | 30 | | | | 50 | | | | |
| trehalose | | 10 | | | | 30 | | | 70 | | 40 | |
| lactose | | | | | | | | | | 30 | | 20 |
| sucrose | | | 50 | | 40 | 50 | 30 | | | | | 15 |
| alanine | | | | 10 | | | | | | | | |
| glycine | | | 10 | | | | 3 | 27 | | 10 | | |
| arginine | | | | 3 | | | | | | | 3 | |
| glutamic acid | | | | 1 | | | | | | | | |
| histidine | | | 3 | | 4 | | | 3 | | | 3 | |
| isoleucine | | | | | | | | | | | | 2 |
| F 68 | surfactant (%) | 0.03 | | | | | | | | | | 0.04 |
| TW-20 | | | 0.005 | | 0.01 | | | | | 0.05 | 0.01 | |
| TW-80 | | | | | | 0.05 | 0.02 | 0.001 | | | | |
| HS 15 | | | | 0.1 | | | | | 0.01 | | | |
| mannitol | supporting agent (mg/mL) | 50 | | 40 | 30 | 20 | 50 | | 20 | 20 | 30 | 50 |
| dextrin | | | | | | | | 10 | | | | |
| dextran | | | 20 | | | | | | | | | |
| phosphate | buffered salt (mM) | | 30 | | | | 25 | | | 20 | | 20 |
| acetate | | | | | 25 | | | | | | | |
| citrate | | 50 | | | | 30 | | | 25 | | | |
| histidine hydrochloride | | | | | 25 | | | 10 | | | 12 | |
| arginine hydrochloride | | | | | | | | | | | 13 | |
| pH value of compositions in Examples | | 6.85 | 7.00 | 6.92 | 6.87 | 6.82 | 6.91 | 6.80 | 6.86 | 6.86 | 6.83 | 6.85 |
| pH value of injection powders in Examples | | 6.85 | 7.10 | 6.92 | 6.93 | 6.82 | 6.95 | 6.80 | 7.20 | 7.05 | 6.83 | 6.85 |

Example 12. Performance Test of the NGF Composition Injection Powders Prepared in Examples 1-11

(1) Test of Appearance, Moisture, Osmotic Pressure, pH, Content and Activity

The NGF composition injection powders prepared in Examples 1-11 and a reference preparation (mouse nerve growth factor for injection, trade name: Sutaisheng, manufactured by the Staidson (Beijing) Biopharmaceuticals Co., Ltd.) are observed for the appearances, respectively, and their moistures, osmotic pressures, pHs, contents and activities are determined. The method of determining the NGF content is carried out according to the method described in Example 1 in Patent No. 200510130348.3, entitled "Method for Determining the Content of Nerve Growth Factor". The activity test method is determined by a cell method, and the detailed method of operation is carried out according to the method of Example 1 in Patent Publication No. CN 103376248A, entitled "Method for Quantitative Determination of Nerve Growth Factor Activity". The experimental results are shown in Table 2.

TABLE 2

Test results of test items in the Examples

Test results of the test items

| Sample | Appearance | Moisture (%) | Osmotic pressure (mOsm/kg) | pH | Average content (%) | Average activity (U/bottle) |
|---|---|---|---|---|---|---|
| Reference preparation | white loose solid blocks | 0.8 | 113 | 6.89 | 98.93 | 20675 |
| Example 1 | white loose solid blocks | 2.5 | 129 | 6.90 | 97.55 | 27139 |
| Example 2 | white loose solid blocks | 2.4 | 142 | 6.96 | 98.61 | 19035 |
| Example 3 | white loose solid blocks | 1.7 | 133 | 6.97 | 100.23 | 17857 |
| Example 4 | white loose solid blocks | 2.3 | 146 | 6.83 | 99.54 | 21944 |
| Example 5 | white loose solid blocks | 2.7 | 142 | 6.89 | 98.01 | 18155 |
| Example 6 | white loose solid blocks | 2.0 | 145 | 6.97 | 99.58 | 19637 |
| Example 7 | white loose solid blocks | 1.9 | 150 | 6.86 | 99.13 | 38015 |
| Example 8 | white loose solid blocks | 2.8 | 158 | 6.88 | 99.42 | 18061 |
| Example 9 | white loose solid blocks | 2.2 | 152 | 6.95 | 99.16 | 19313 |
| Example 10 | white loose solid blocks | 2.5 | 139 | 6.95 | 98.83 | 17523 |
| Example 11 | white loose solid blocks | 1.3 | 142 | 6.93 | 97.08 | 8159 |

As can be seen from Table 2, the indexes of the NGF composition injection powders prepared in the present invention all meet the quality standard requirements.

(2) Stable pH Range Screening

According to the formulation composition of Example 2, 3 NGF compositions are formulated, wherein the total amount of phosphate is kept constant and the amounts of the NaH2PO4.H2O and Na2HPO4 are adjusted so that the pH values of the NGF compositions are 6.0, 6.8 and 7.4, respectively, then filled into penicillin bottles, respectively, and lyophilized to prepare sterile injection powder. Samples are taken, and an appropriate amount of sterile water for injection is added to formulate into solutions. Under room temperature condition, the solutions are observed for the appearance and determined for the pH value, the content and the activity are measured at 0, 4, 8, 12 and 24 hours, respectively. The results are shown in the following table.

TABLE 3

Stable pH range screening results of NGF compositions

| Sample name | Placing time (h) | Appearance | pH | Average content (%) | Average activity (%) |
|---|---|---|---|---|---|
| Sample 1 (pH 6.0) | 0 | Colorless clear solution | 6.08 | 99.87 | 18881 |
| | 4 | Colorless clear solution | 6.04 | 99.32 | 19233 |
| | 8 | Colorless clear solution | 6.02 | 98.79 | 18589 |
| | 12 | Colorless clear solution | 5.98 | 98.03 | 18621 |
| | 24 | Colorless clear solution | 6.08 | 97.52 | 18026 |
| Sample 2 (pH 6.8) | 0 | Colorless clear solution | 6.84 | 100.68 | 20152 |
| | 4 | Colorless clear solution | 6.83 | 100.19 | 19839 |

TABLE 3-continued

Stable pH range screening results of NGF compositions

| Sample name | Placing time (h) | Appearance | pH | Average content (%) | Average activity (%) |
|---|---|---|---|---|---|
| | 8 | Colorless clear solution | 6.83 | 99.81 | 21088 |
| | 12 | Colorless clear solution | 6.86 | 99.75 | 19055 |
| | 24 | Colorless clear solution | 6.84 | 99.43 | 19573 |

TABLE 3-continued

Stable pH range screening results of NGF compositions

| Sample name | Placing time (h) | Appearance | pH | Average content (%) | Average activity (%) |
|---|---|---|---|---|---|
| Sample 3 (pH 7.4) | 0 | Colorless clear solution | 7.40 | 100.53 | 18335 |
| | 4 | Colorless clear solution | 7.38 | 100.84 | 19236 |
| | 8 | Colorless clear solution | 7.38 | 99.98 | 19508 |
| | 12 | Colorless clear solution | 7.37 | 99.23 | 18123 |
| | 24 | Colorless clear solution | 7.42 | 98.56 | 17526 |

It can be seen from the above table data that after the three NGF compositions with different pH values are placed at room temperature for 24 h, the indexes all have no significant changes than at 0 h, all meet the quality standard requirements, indicating that under room temperature condition, the sample solutions can remain stable for 24 h in a range of pH 6.0-7.4, preferably at pH 6.8.

(3) Stability Test

A. Accelerated Stability Test

According to the requirements of "Technical Guidelines for Research on Stability of Biological Products", the samples of the reference preparation (Sutaisheng) and the subpackaged NGF composition injection powders prepared in the Examples are examined for an accelerated stability for 0-6 months under conditions of 25° C., RH 60±10%. The samples are observed for the appearances, and determined for the moistures, osmotic pressures, pH values, contents and activities. The results are shown in Table 4 and FIG. 1 (the change curve of average content over time), and FIG. 2 (the change curve of average activity over time).

TABLE 4

Accelerated stability test results of the NGF composition injection powders and the reference preparation

| Time (month) | Sample | Appearance | Moisture (%) | Osmotic pressure (mOsm/kg) | pH | Average content (%) | Average activity (U/bottle) |
|---|---|---|---|---|---|---|---|
| 0 | Reference preparation | white loose solid blocks | 0.8 | 113 | 6.89 | 98.93 | 20675 |
| | Example 1 | white loose solid blocks | 2.5 | 129 | 6.85 | 97.55 | 27139 |
| | Example 2 | white loose solid blocks | 2.4 | 142 | 7.10 | 98.61 | 19035 |
| | Example 3 | white loose solid blocks | 1.7 | 133 | 6.92 | 100.23 | 17857 |
| | Example 4 | white loose solid blocks | 2.3 | 146 | 6.93 | 99.54 | 21944 |
| | Example 5 | white loose solid blocks | 2.7 | 142 | 6.82 | 98.01 | 18155 |
| | Example 6 | white loose solid blocks | 2.0 | 145 | 6.95 | 99.58 | 19637 |
| | Example 7 | white loose solid blocks | 1.9 | 150 | 6.80 | 99.13 | 38015 |
| | Example 8 | white loose solid blocks | 2.8 | 158 | 7.20 | 99.42 | 18061 |
| | Example 9 | white loose solid blocks | 2.2 | 152 | 7.05 | 99.16 | 19313 |
| | Example 10 | white loose solid blocks | 2.5 | 139 | 6.83 | 98.83 | 17523 |
| | Example 11 | white loose solid blocks | 1.3 | 142 | 6.85 | 97.08 | 8159 |
| 1 | Reference preparation | white loose solid blocks | 0.9 | 108 | 6.92 | 95.68 | 19736 |
| | Example 1 | white loose solid blocks | 2.4 | 125 | 6.87 | 96.29 | 27628 |
| | Example 2 | white loose solid blocks | 2.4 | 140 | 7.08 | 97.66 | 18558 |
| | Example 3 | white loose solid blocks | 1.6 | 137 | 6.90 | 98.87 | 17233 |
| | Example 4 | white loose solid blocks | 2.4 | 142 | 6.94 | 99.21 | 22122 |
| | Example 5 | white loose solid blocks | 2.5 | 140 | 6.86 | 96.58 | 17521 |
| | Example 6 | white loose solid blocks | 2.1 | 139 | 6.93 | 99.18 | 19547 |
| | Example 7 | white loose solid blocks | 1.8 | 152 | 6.82 | 98.19 | 37217 |
| | Example 8 | white loose solid blocks | 2.7 | 162 | 7.18 | 99.76 | 19125 |
| | Example 9 | white loose solid blocks | 2.3 | 147 | 7.05 | 98.89 | 19305 |
| | Example 10 | white loose solid blocks | 2.6 | 143 | 6.80 | 97.49 | 17011 |

TABLE 4-continued

Accelerated stability test results of the NGF composition injection powders and the reference preparation

| Time (month) | Sample | Appearance | Moisture (%) | Osmotic pressure (mOsm/kg) | pH | Average content (%) | Average activity (U/bottle) |
|---|---|---|---|---|---|---|---|
| | Example 11 | white loose solid blocks | 1.5 | 139 | 6.85 | 95.65 | 8702 |
| 2 | Reference preparation | white loose solid blocks | 0.9 | 112 | 6.86 | 94.48 | 19516 |
| | Example 1 | white loose solid blocks | 2.5 | 126 | 6.88 | 94.78 | 26026 |
| | Example 2 | white loose solid blocks | 2.3 | 145 | 7.11 | 96.33 | 17927 |
| | Example 3 | white loose solid blocks | 1.7 | 130 | 6.94 | 96.85 | 16356 |
| | Example 4 | white loose solid blocks | 2.2 | 143 | 6.91 | 98.57 | 21228 |
| | Example 5 | white loose solid blocks | 2.6 | 145 | 6.86 | 94.22 | 17019 |
| | Example 6 | white loose solid blocks | 2.0 | 140 | 6.97 | 98.52 | 19313 |
| | Example 7 | white loose solid blocks | 1.8 | 151 | 6.83 | 96.70 | 35982 |
| | Example 8 | white loose solid blocks | 2.6 | 157 | 7.19 | 99.01 | 17893 |
| | Example 9 | white loose solid blocks | 2.3 | 156 | 7.08 | 98.15 | 18967 |
| | Example 10 | white loose solid blocks | 2.6 | 141 | 6.86 | 96.05 | 16537 |
| | Example 11 | white loose solid blocks | 1.4 | 144 | 6.87 | 93.72 | 7575 |
| 3 | Reference preparation | white loose solid blocks | 1.0 | 109 | 6.93 | 91.61 | 17245 |
| | Example 1 | white loose solid blocks | 2.3 | 131 | 6.86 | 92.89 | 25133 |
| | Example 2 | white loose solid blocks | 2.5 | 140 | 7.10 | 94.72 | 17232 |
| | Example 3 | white loose solid blocks | 1.8 | 135 | 6.91 | 94.97 | 15702 |
| | Example 4 | white loose solid blocks | 2.4 | 143 | 6.93 | 97.38 | 20152 |
| | Example 5 | white loose solid blocks | 2.5 | 145 | 6.83 | 93.56 | 16628 |
| | Example 6 | white loose solid blocks | 1.9 | 141 | 6.94 | 97.75 | 18201 |
| | Example 7 | white loose solid blocks | 1.7 | 152 | 6.81 | 94.22 | 34261 |
| | Example 8 | white loose solid blocks | 2.6 | 160 | 7.20 | 98.31 | 17335 |
| | Example 9 | white loose solid blocks | 2.1 | 157 | 7.07 | 97.62 | 18413 |
| | Example 10 | white loose solid blocks | 2.4 | 141 | 6.84 | 94.53 | 15991 |
| | Example 11 | white loose solid blocks | 1.4 | 138 | 6.85 | 91.58 | 7523 |
| 6 | Reference preparation | white loose solid blocks | 1.0 | 115 | 6.83 | 90.58 | 17023 |
| | Example 1 | white loose solid blocks | 2.6 | 130 | 6.84 | 89.93 | 23209 |
| | Example 2 | white loose solid blocks | 2.4 | 141 | 7.10 | 92.63 | 16653 |
| | Example 3 | white loose solid blocks | 1.7 | 130 | 6.93 | 92.19 | 15124 |
| | Example 4 | white loose solid blocks | 2.4 | 143 | 6.95 | 96.31 | 19985 |
| | Example 5 | white loose solid blocks | 2.6 | 140 | 6.83 | 92.65 | 16226 |
| | Example 6 | white loose solid blocks | 2.1 | 146 | 6.94 | 95.96 | 17838 |
| | Example 7 | white loose solid blocks | 1.8 | 148 | 6.83 | 91.28 | 33129 |
| | Example 8 | white loose solid blocks | 2.9 | 157 | 7.19 | 96.39 | 16926 |
| | Example 9 | white loose solid blocks | 2.3 | 153 | 7.06 | 96.78 | 18169 |

TABLE 4-continued

Accelerated stability test results of the NGF composition
injection powders and the reference preparation

| Time (month) | Sample | Appearance | Moisture (%) | Osmotic pressure (mOsm/kg) | pH | Average content (%) | Average activity (U/bottle) |
|---|---|---|---|---|---|---|---|
| | Example 10 | white loose solid blocks | 2.4 | 141 | 6.85 | 93.72 | 15585 |
| | Example 11 | white loose solid blocks | 1.2 | 143 | 6.87 | 89.19 | 7029 |

As can be seen from FIG. 1, the average content of NGF in the reference preparation and the NGF composition injection powders prepared in the Examples presents a reduction tendency over time under accelerated conditions (25° C., RH 60±10%), wherein the reduction speed in the average content of NGF in the reference preparation is significantly greater than that of the compositions of the Examples of the present invention. As can be seen from the results in Table 4, the appearances, moistures, pH values and osmotic pressures of the samples are not significantly changed under the accelerated conditions (25° C., RH 60±10%) for 6 months, but the content of the reference preparation reduces by about 10.5%, the reduction rates in the contents of the NGF composition injection powders of Examples 1 to 11 are 7.8%, 6.1%, 8.0%, 3.2%, 5.5%, 3.6%, 7.9%, 3.0%, 2.4%, 5.2% and 8.1%, respectively, indicating that the stability of the Examples of the present invention is superior to the reference preparation under accelerated conditions. Among them, the reduction rates in the compositions of Examples 4, 6, 8 and 9 are 3.2%, 3.6%, 3.0%, 2.4%, respectively, far below that of the reference preparation, indicating that the stability of the compositions of Examples 4, 6, 8 and 9 is significantly superior to that of the reference preparation under the accelerated conditions.

Figure 2:
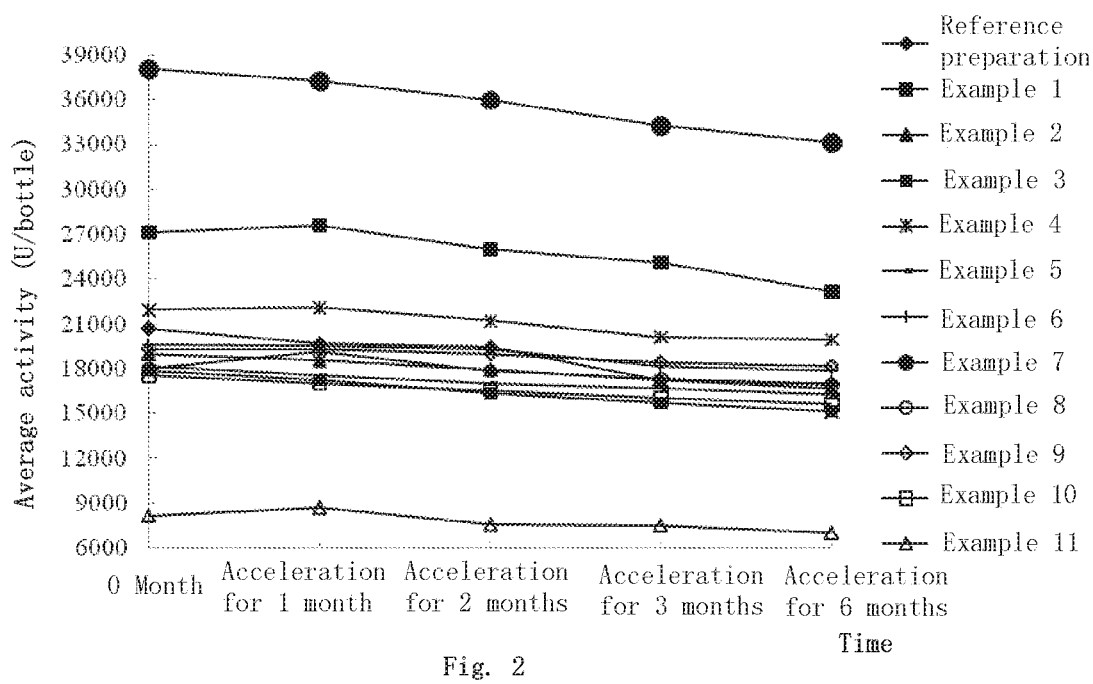
FIG. 2 shows the change curve of the average activity over time of the NGF composition injection powders prepared in the Examples and the reference preparation, under the accelerated condition (25° C., RH 60±10%).

As can be seen from FIG. 2, the average activity of NGF in the reference preparation and the subpackaged NGF composition injection powders prepared in the Examples presents a reduction tendency over time as a whole under accelerated conditions (25° C., RH 60±10%), wherein the activity of the reference preparation reduces rapidly after two months of acceleration. As can be seen from the results in Table 4, the appearances, moistures, pH values and osmotic pressures of the samples are not significantly changed under accelerated conditions (25° C., RH 60±10%) for 6 months, but the activity of the reference preparation reduces by 17.7%, the activities of the NGF composition injection powders of Examples 1 to 11 reduce by 14.5%, 12.5%, 15.3%, 8.9%, 10.6%, 9.2%, 12.9%, 6.3%, 5.9%, 11.1% and 13.8% respectively, indicating that the stability of the Examples of the present invention is superior to the reference preparation under accelerated conditions. Among them, the reduction rates in the activities of the compositions of Examples 4, 6, 8 and 9 are 8.9%, 9.2%, 6.3% and 5.9%, respectively, far below that of the reference preparation, indicating that the stability of the compositions of Examples 4, 6, 8 and 9 is significantly superior to that of the reference preparation under the accelerated conditions.

B. Long-Term Stability Test

According to the requirements of "Technical Guidelines for Research on Stability of Biological Products", the samples of the reference preparation (Sutaisheng) and the subpackaged NGF injection powders prepared in the Examples 4, 6, 8 and 9 are examined for a long-term stability for 0-12 months under condition of 6±2° C. The samples are observed for the appearances, and determined for the moistures, osmotic pressures, pH values, contents and activities. The results are shown in Table 5, and FIG. 3 (the change curve of average content over time) and FIG. 4 (the change curve of average activity over time).

TABLE 5

Long-term stability test results of the NGF composition
injection powders and the reference preparation

| time (month) | Sample | Appearance | Moisture (%) | Osmotic pressure (mOsm/kg) | pH | Average content (%) | Average activity (U/bottle) |
|---|---|---|---|---|---|---|---|
| 0 | Reference preparation | white loose solid blocks | 0.8 | 113 | 6.89 | 98.93 | 20675 |
| | Example 1 | white loose solid blocks | 2.5 | 129 | 6.85 | 97.55 | 27139 |
| | Example 2 | white loose solid blocks | 2.4 | 142 | 7.10 | 98.61 | 19035 |
| | Example 3 | white loose solid blocks | 1.7 | 133 | 6.92 | 100.23 | 17857 |
| | Example 4 | white loose solid blocks | 2.3 | 146 | 6.93 | 99.54 | 21944 |
| | Example 5 | white loose solid blocks | 2.7 | 142 | 6.82 | 98.01 | 18155 |
| | Example 6 | white loose solid blocks | 2.0 | 145 | 6.95 | 99.58 | 19637 |
| | Example 7 | white loose solid blocks | 1.9 | 150 | 6.80 | 99.13 | 38015 |
| | Example 8 | white loose solid blocks | 2.8 | 158 | 7.20 | 99.42 | 18061 |

TABLE 5-continued

Long-term stability test results of the NGF composition
injection powders and the reference preparation

| time (month) | Sample | Appearance | Moisture (%) | Osmotic pressure (mOsm/kg) | pH | Average content (%) | Average activity (U/bottle) |
|---|---|---|---|---|---|---|---|
| | Example 9 | white loose solid blocks | 2.2 | 152 | 7.05 | 99.16 | 19313 |
| | Example 10 | white loose solid blocks | 2.5 | 139 | 6.83 | 98.83 | 17523 |
| | Example 11 | white loose solid blocks | 1.3 | 142 | 6.85 | 97.08 | 8159 |
| 3 | Reference preparation | white loose solid blocks | 1.0 | 108 | 6.89 | 96.98 | 19519 |
| | Example 1 | white loose solid blocks | 2.4 | 131 | 6.87 | 96.89 | 28021 |
| | Example 2 | white loose solid blocks | 2.3 | 143 | 7.09 | 98.02 | 18863 |
| | Example 3 | white loose solid blocks | 1.6 | 135 | 6.95 | 99.88 | 17217 |
| | Example 4 | white loose solid blocks | 2.3 | 144 | 6.94 | 99.16 | 22014 |
| | Example 5 | white loose solid blocks | 2.6 | 145 | 6.86 | 97.56 | 17796 |
| | Example 6 | white loose solid blocks | 2.1 | 141 | 6.98 | 99.29 | 19836 |
| | Example 7 | white loose solid blocks | 1.8 | 152 | 6.83 | 98.85 | 37112 |
| | Example 8 | white loose solid blocks | 2.7 | 156 | 7.18 | 99.15 | 19518 |
| | Example 9 | white loose solid blocks | 2.3 | 151 | 7.07 | 99.45 | 20557 |
| | Example 10 | white loose solid blocks | 2.5 | 142 | 6.85 | 98.08 | 17019 |
| | Example 11 | white loose solid blocks | 1.5 | 140 | 6.84 | 95.99 | 8531 |
| 6 | Reference preparation | white loose solid blocks | 0.8 | 113 | 6.91 | 95.39 | 18815 |
| | Example 1 | white loose solid blocks | 2.5 | 128 | 6.87 | 95.18 | 26562 |
| | Example 2 | white loose solid blocks | 2.6 | 140 | 7.11 | 96.53 | 18025 |
| | Example 3 | white loose solid blocks | 1.8 | 135 | 6.93 | 97.79 | 16875 |
| | Example 4 | white loose solid blocks | 2.4 | 143 | 6.92 | 97.99 | 21233 |
| | Example 5 | white loose solid blocks | 2.6 | 145 | 6.85 | 96.63 | 17528 |
| | Example 6 | white loose solid blocks | 2.2 | 148 | 6.94 | 98.27 | 19126 |
| | Example 7 | white loose solid blocks | 1.8 | 153 | 6.82 | 96.94 | 36213 |
| | Example 8 | white loose solid blocks | 2.9 | 154 | 7.20 | 98.55 | 18543 |
| | Example 9 | white loose solid blocks | 2.0 | 155 | 7.05 | 98.88 | 19588 |
| | Example 10 | white loose solid blocks | 2.4 | 141 | 6.84 | 96.72 | 16751 |
| | Example 11 | white loose solid blocks | 1.5 | 140 | 6.86 | 94.33 | 7852 |
| 9 | Reference preparation | white loose solid blocks | 0.9 | 111 | 6.91 | 93.98 | 18502 |
| | Example 1 | white loose solid blocks | 2.5 | 131 | 6.87 | 93.50 | 25301 |
| | Example 2 | white loose solid blocks | 2.5 | 140 | 7.09 | 94.99 | 17665 |
| | Example 3 | white loose solid blocks | 1.8 | 129 | 6.93 | 96.11 | 16430 |
| | Example 4 | white loose solid blocks | 2.2 | 142 | 6.95 | 97.43 | 20956 |
| | Example 5 | white loose solid blocks | 2.6 | 146 | 6.84 | 94.71 | 17013 |
| | Example 6 | white loose solid blocks | 1.9 | 143 | 6.94 | 97.83 | 18798 |
| | Example 7 | white loose solid blocks | 1.8 | 145 | 6.82 | 95.61 | 35128 |

TABLE 5-continued

Long-term stability test results of the NGF composition injection powders and the reference preparation

| time (month) | Sample | Appearance | Moisture (%) | Osmotic pressure (mOsm/kg) | pH | Average content (%) | Average activity (U/bottle) |
|---|---|---|---|---|---|---|---|
| | Example 8 | white loose solid blocks | 2.7 | 152 | 7.19 | 98.11 | 17991 |
| | Example 9 | white loose solid blocks | 2.3 | 150 | 7.06 | 98.02 | 18862 |
| | Example 10 | white loose solid blocks | 2.5 | 142 | 6.86 | 95.65 | 16253 |
| | Example 11 | white loose solid blocks | 1.5 | 140 | 6.84 | 93.05 | 7510 |
| 12 | Reference preparation | white loose solid blocks | 0.8 | 109 | 6.86 | 92.32 | 18033 |
| | Example 1 | white loose solid blocks | 2.5 | 127 | 6.88 | 91.41 | 24181 |
| | Example 2 | white loose solid blocks | 2.5 | 144 | 7.10 | 93.58 | 17206 |
| | Example 3 | white loose solid blocks | 1.7 | 135 | 6.94 | 94.02 | 16026 |
| | Example 4 | white loose solid blocks | 2.2 | 141 | 6.95 | 96.72 | 20889 |
| | Example 5 | white loose solid blocks | 2.8 | 144 | 6.82 | 93.03 | 16582 |
| | Example 6 | white loose solid blocks | 2.1 | 146 | 6.95 | 96.61 | 18586 |
| | Example 7 | white loose solid blocks | 1.8 | 149 | 6.81 | 93.12 | 34518 |
| | Example 8 | white loose solid blocks | 2.7 | 156 | 7.20 | 96.87 | 17366 |
| | Example 9 | white loose solid blocks | 2.2 | 153 | 7.04 | 97.18 | 18653 |
| | Example 10 | white loose solid blocks | 2.5 | 141 | 6.84 | 94.43 | 16111 |
| | Example 11 | white loose solid blocks | 1.2 | 140 | 6.85 | 91.22 | 7323 |

Figure 3:
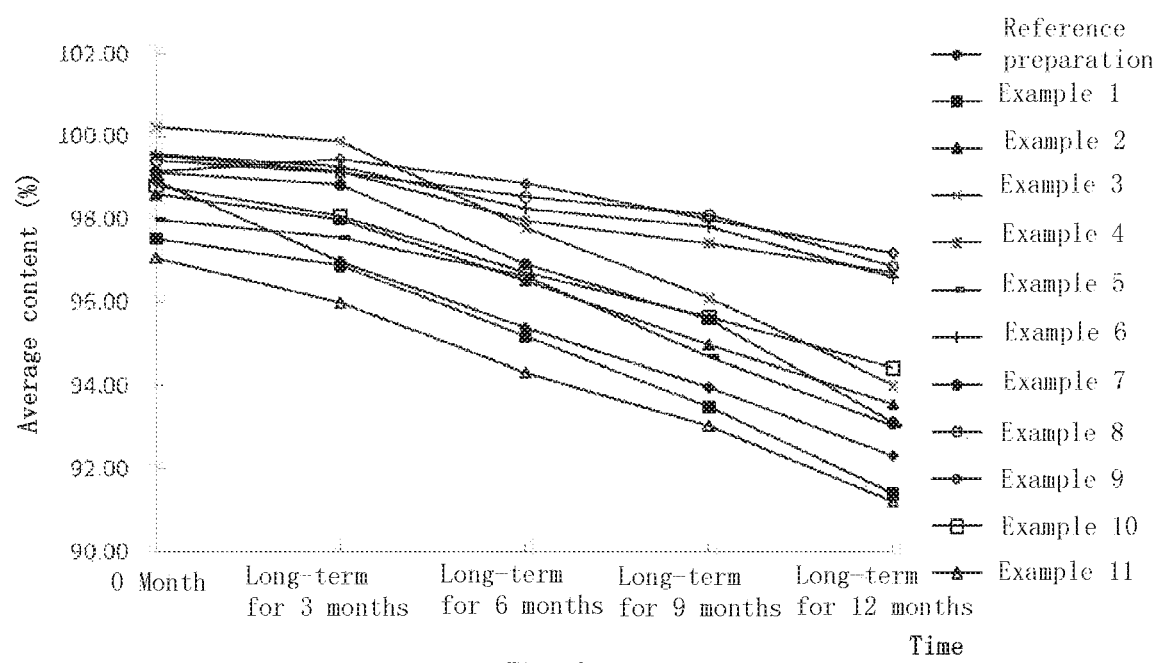
FIG. 3 shows the change curve of the average content of NGF over time in the NGF composition injection powders prepared in the Examples and the reference preparation, under the long-term stability condition (6±2° C.).

As can be seen from FIG. 3, the average content of NGF in the reference preparation and the subpackaged NGF composition injection powders prepared in the Examples presents a reduction tendency over time under the long-term stability condition (6±2° C.), wherein the reduction speed in the average content of NGF in the reference preparation is significantly greater than that of the compositions of the Examples of the present invention. As can be seen from the results in Table 5, the appearances, moistures, pH values and osmotic pressures of the samples are not significantly changed under the long-term condition (6±2° C.) for 12 months, but the content of the reference preparation reduces by about 6.7%, the reduction rates in the contents of the NGF composition injection powders of Examples 1 to 11 are 6.3%, 5.1%, 6.2%, 2.8%, 5.1%, 3.0%, 6.1%, 2.6%, 2.0%, 4.5% and 6.0%, respectively, indicating that the stability of the Examples of the present invention is superior to the reference preparation under the long-term stability condition (6±2° C.). Among them, the reduction rates in the compositions of Examples 4, 6, 8 and 9 are 2.8%, 3.0%, 2.6%, and 2.0%, respectively, far below that of the reference preparation, indicating that the stability of the compositions of Examples 4, 6, 8 and 9 is significantly superior to that of the reference preparation under the long-term condition.

Figure 4:
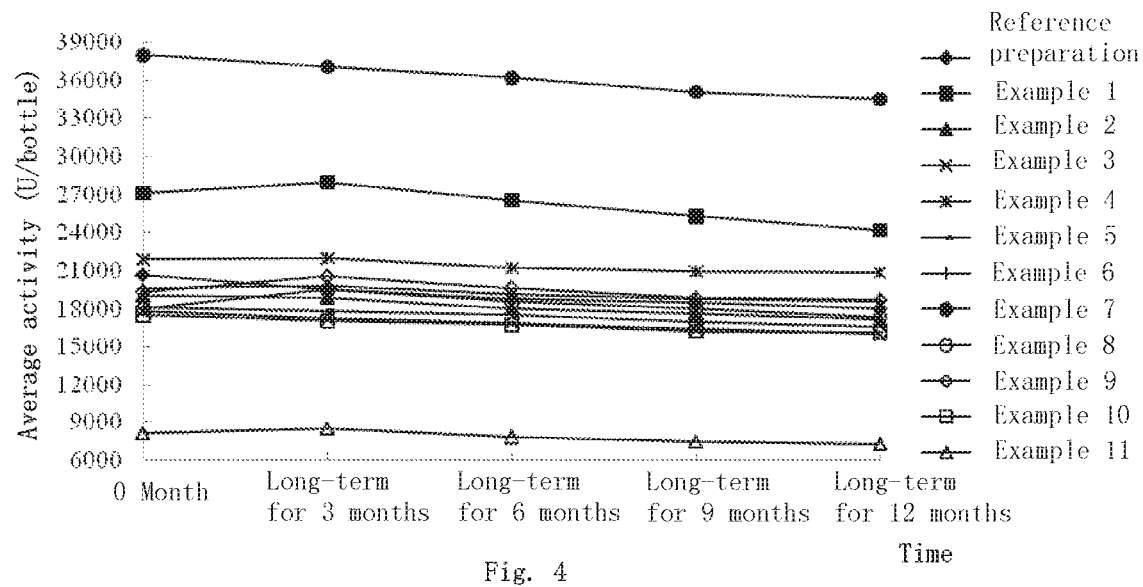
FIG. 4 shows the change curve of the average activity over time of the NGF composition injection powders prepared in the Examples and the reference preparation, under the long-term stability condition (6±2° C.).

As can be seen from FIG. 4, the average activity of NGF in the reference preparation and the subpackaged NGF composition injection powders prepared in the Examples presents a reduction tendency over time as a whole under the long-term stability condition (6±2° C.), wherein the reduction speed in the activity of the reference preparation is greater than that of Examples of the present invention. As can be seen from the results in Table 4, the appearances, moistures, pH values and osmotic pressures of the samples are not significantly changed under the long-term condition (6±2° C.) for 12 months, but the activity of the reference preparation reduces by 12.8%, the activities of the NGF composition injection powders of Examples 1 to 11 reduce by 10.9%, 9.6%, 10.3%, 4.8%, 8.7%, 5.4%, 9.2%, 3.8%, 3.4%, 8.1% and 10.2% respectively, indicating that the stability of the Examples of the present invention is superior to the reference preparation under the long-term stability condition (6±2° C.). Among them, the activities of the compositions of Examples 4, 6, 8 and 9 reduce by 4.8%, 5.4%, 3.8%, and 3.4%, respectively, far below that of the reference preparation, indicating that the stability of the compositions of Examples 4, 6, 8 and 9 is significantly superior to that of the reference preparation under the long-term condition.

(4) Clinical Evaluation

A total of 271 patients with optic nerve injury are subjected to a 12-weeks clinical trial by the multicenter non-randomized controlled clinical study design; all the subjects are 14 years or older, and are able to communicate well with the investigators, understand and comply with clinical trial requirements, and sign an informed consent.

Subject condition: 14 years or older.

Gender: male or female.

Subject source: 409 patients with optic nerve injury caused by various causes from various ophthalmic research units being enrolled.

Injury cause: 136 cases of first injury (136 eyes), 152 cases of car accident (152 eyes), 73 cases of physical hit injury (73 eyes), 49 cases of eye explosive injury (49 eyes). All cases are not accompanied by eyeball rupture and damage caused by the optic nerve compression due to orbital fractures.

Treatment method: the treatment group is injected with the reference preparation and the NGF compositions of the present invention by intramuscular injection (water for injection) once a day with each 30 μg, and all cases are administered continuously for 12 weeks. The placebo group is treated with a negative control (with no active ingredient, and the remaining excipients being the same to those in the NGF compositions).

The treatment group comprises 271 cases (271 eyes), with age of 18 to 63 years, and the average age of 34.2 years; 189 males (189 eyes), 82 females (82 eyes); 147 eyes in the right eye, 124 eyes in the left eye. The placebo group comprises 138 patients (138 eyes), with age of 13-55 years, and the average age of 33.9 years, 96 males (96 eyes), 42 females (42 eyes), 45 eyes in the right eye and 93 eyes in the left eye.

Grouping design: grouping is shown in the following table:

TABLE 6

Grouping of clinical trial and number of subjects

| Test group | Trial grouping and number of subjects (person) | | |
| --- | --- | --- | --- |
| | Placebo group | Reference preparation group | NGF composition group |
| Fist injury | 46 | 45 | 45 |
| Car accident | 50 | 51 | 51 |
| Physical hit injury | 25 | 24 | 24 |
| Explosive injury | 17 | 16 | 16 |
| Number of subjects in each group | 138 | 135 | 136 |

Note:
the nerve growth factor composition prepared in Example 9 is used, the same below.

Clinical common adverse reaction evaluation: the placebo group, the reference preparation group and the NGF composition group are administered, respectively, and observed for the symptom and incidence of the adverse reactions in each group, and the results are shown in the following table.

TABLE 7

NGF clinical common adverse reactions

| Adverse reaction symptom | Placebo group (N = 138) | Reference preparation group (N = 135) | NGF composition group (N = 136) |
| --- | --- | --- | --- |
| Local pain | 2 (1.4) | 11 (8.1)* | 8 (5.9)*# |
| Urticaria | 1 (0.7) | 4 (3.0)* | 2 (1.5)*# |
| Dizziness | 1 (0.7) | 7 (5.2)* | 5 (3.7)*# |
| Insomnia | 7 (5.1) | 3 (2.2)* | 1 (0.7)*# |
| Conjunctival congestion | 0 (0) | 1 (0.7)* | 1 (0.7)* |

Note:
*indicates that there is a significant difference compared with the placebo group (P < 0.05),
indicates that there is a significant difference compared with the reference preparation group (P < 0.05).

It can be seen from the above table that, compared with the placebo group, the main adverse reactions of the NGF compositions prepared in the present invention are local pain, urticaria and dizziness, and compared with the reference preparation group, the NGF compositions prepared in the present invention can significantly alleviate the adverse reactions, such as local pain, urticaria, dizziness, etc.

Clinical efficacy: the placebo group, the reference preparation group and the NGF composition group are administered, respectively, and observed for the clinical efficacy in each group. The results are shown in the following table.

TABLE 8

Comparison of NGF clinical efficacy

| Clinical efficacy | Placebo group (N = 138) | Reference preparation group (N = 135) | NGF composition group (N = 136) |
| --- | --- | --- | --- |
| Recovery | 3 (2.2) | 82 (60.7) | 88 (64.7) |
| Effective | 11 (8.0) | 24 (17.8) | 29 (21.3) |
| Alleviated | 9 (6.5) | 19 (14.1) | 17 (12.5) |
| Ineffective | 115 (83.3) | 10 (7.4) | 2 (1.5) |

The clinical efficacy in the above table is evaluated using the following clinical efficacy evaluation criteria:
①Recovery: the vision recovers to 1.0 or more, and dark spots in the central visual field disappear;
②Effective: the vision increases by 4 lines or more, dark spots in the central visual field reduce or the absolute dark spots become relative dark spots;
③Alleviated: the vision increases by 2 lines or more, and there is no change in visual field;
④Ineffective: the vision and visual field are the same as before the treatment, or decline.

It can be seen from the above table that, compared with the placebo group, the NGF compositions and the injection powders thereof of the present invention can be effective in treating optic nerve injury caused by various causes, have the comprehensive efficiency of the treatment of optic nerve injury that is superior to that of the reference preparation group, can significantly reduce the incidence of the adverse reactions, and have good clinical therapeutic effect.

While the present invention has been described in detail by way of general description, particular embodiments and examples, various modifications and improvements may be made by those skilled in the art on the basis of the present invention without departing from the spirit of the invention and such modifications or improvements are all within the scope according to the present invention.

INDUSTRIAL APPLICATION

The nerve growth factor composition injection powders prepared in the present invention retain good stability in preparation, transportation and storage processes: (1) in the preparation process: after the nerve growth factor composition injection powders prepared in the present invention are placed at room temperature for 24 hours, the content and activity of the NGF therein have no significant change; (2) compared with the reference preparation, in the conventional (6±2° C.) transportation and storage processes, the NGF composition injection powders of the present invention has an effective content reduction of only 2.0%-6.3%, preferably 2.0%-3.0%, and an activity reduction of only 3.4%-10.9%, after being placed for 12 months, thereby having the excellent stability.

The nerve growth factor composition injection powders prepared in the present invention can significantly reduce the incidence of the adverse reactions in the clinical trial, have good clinical therapeutic effect, and have better clinical medication safety and quality controllability as compared with the existing reference preparation.

The present invention has the following beneficial effects:

(1) the nerve growth factor compositions and the injection powders of the present invention can avoid the potential risk resulting from the virus or other unknown components carried in albumin by using a disaccharide or a combination of a disaccharide and an amino acid instead of albumin as a stabilizer.

(2) the nerve growth factor composition injection powders of the present invention not only have protective effect on mouse-derived nerve growth factor (mNGF), but also can ensure the good stability of the human-derived nerve growth factor (hNGF) and the recombinant human nerve growth factor (rhNGF) in the preparation, transportation and storage processes, and have better clinical medication safety and quality controllability.

(3) the nerve growth factor compositions and the injection powders of the present invention have definite ingredients, are easily qualitative and quantitative, and the stabilizer used therein has a high purity, a wide source and easy long-term mass production, which facilitate the cost control and the product quality improvement.

The invention claimed is:

1. An albumin-free nerve growth factor composition, wherein the albumin-free nerve growth factor composition comprises the following components:
   a nerve growth factor at a mass-volume concentration of 50 μg/mL;
   a disaccharide stabilizer at a mass-volume concentration of 30 mg/mL;
   an amino acid stabilizer, including at least one of isoleucine and glutamic acid, at a mass-volume concentration of 10 mg/mL;
   a surfactant at a mass-volume concentration of 0.5 mg/mL;
   a supporting agent, including mannitol, dextrin, or dextran, at a mass-volume concentration of 20 mg/mL;
   a pH buffer for maintaining the albumin-free nerve growth factor composition at a pH value of 6.0 to 7.4, wherein a mole concentration of the pH buffer is 20 mM;
   and a solvent, wherein the solvent is water.

2. The albumin-free nerve growth factor composition according to claim 1, wherein the disaccharide stabilizer is at least one of maltose, trehalose, sucrose, and lactose.

3. The albumin-free nerve growth factor composition according to claim 1, wherein the amino acid stabilizer further includes at least one of alanine, glycine, arginine, and histidine.

4. The albumin-free nerve growth factor composition according to claim 3, wherein the amino acid stabilizer further includes histidine and arginine in a ratio of 12:13.

5. The albumin-free nerve growth factor composition according to claim 1, wherein the disaccharide stabilizer and the amino acid stabilizer are any one of the following groups:
   lactose, sucrose, and isoleucine; and
   maltose, alanine, arginine, and glutamic acid.

6. The albumin-free nerve growth factor composition according to claim 1, wherein the surfactant is a nonionic surfactant.

7. A method for preparation of an albumin-free nerve growth factor composition injection powder, wherein the albumin-free nerve growth factor composition according to claim 1 is lyophilized to obtain the albumin-free nerve growth factor composition injection powder.

8. An albumin-free nerve growth factor composition injection powder prepared by the method according to claim 7.

9. The albumin-free nerve growth factor composition according to claim 1, wherein a water content is 2.0-2.8%.

10. An albumin-free nerve growth factor composition, wherein the albumin-free nerve growth factor composition comprises the following components:
    a mass-volume concentration of a nerve growth factor is 50 μg/mL;
    a mass-volume concentration of a disaccharide stabilizer is 30 mg/mL;
    a mass-volume concentration of an amino acid stabilizer is 3 mg/mL;
    a mass-volume concentration of a surfactant is 0.2 mg/mL;
    a mass-volume concentration of a supporting agent is 50 mg/mL; and
    a mole concentration of a pH buffer is 25 mM.

11. An albumin-free nerve growth factor composition, wherein the albumin-free nerve growth factor composition comprises the following components:
    a mass-volume concentration of a nerve growth factor is 50 μg/mL;
    a mass-volume concentration of a disaccharide stabilizer is 30 mg/mL;
    a mass-volume concentration of an amino acid stabilizer is 10 mg/mL;
    a mass-volume concentration of a surfactant is 0.5 mg/mL;
    a mass-volume concentration of a supporting agent is 20 mg/mL; and
    a mole concentration of a pH buffer is 20 mM.

12. An albumin-free nerve growth factor composition, wherein the albumin-free nerve growth factor composition comprises the following components:
    a mass-volume concentration of a nerve growth factor is 60 μg/mL;
    a mass-volume concentration of a disaccharide stabilizer is 40 mg/mL;
    a mass-volume concentration of an amino acid stabilizer is 4 mg/mL;
    a mass-volume concentration of a surfactant is 0.1 mg/mL;
    a mass-volume concentration of a supporting agent is 30 mg/mL; and
    a mole concentration of a pH buffer is 25 mM.

* * * * *